United States Patent
Brown et al.

(10) Patent No.: US 11,749,406 B2
(45) Date of Patent: Sep. 5, 2023

(54) SPINE SEGMENTATION SYSTEM

(71) Applicant: Siemens Healthcare GmbH, Erlangen (DE)

(72) Inventors: Kevin Brown, New York, NY (US); Matthias Wolf, Coatesville, PA (US)

(73) Assignee: Siemens Healthcare GmbH, Erlangen (DE)

( * ) Notice: Subject to any disclaimer, the term of this patent is extended or adjusted under 35 U.S.C. 154(b) by 195 days.

(21) Appl. No.: 16/947,844

(22) Filed: Aug. 20, 2020

(65) Prior Publication Data

US 2021/0056354 A1    Feb. 25, 2021

Related U.S. Application Data

(60) Provisional application No. 62/890,801, filed on Aug. 23, 2019.

(51) Int. Cl.
| | |
|---|---|
| *G06K 9/00* | (2022.01) |
| *G16H 50/20* | (2018.01) |
| *G06T 15/08* | (2011.01) |
| *G06T 7/30* | (2017.01) |
| *G06T 7/11* | (2017.01) |
| *G06T 11/00* | (2006.01) |
| *G06N 3/08* | (2023.01) |
| *G16H 30/40* | (2018.01) |
| *G06F 18/21* | (2023.01) |
| *G06V 10/82* | (2022.01) |
| *G06V 10/44* | (2022.01) |

(52) U.S. Cl.
CPC .......... *G16H 50/20* (2018.01); *G06F 18/2163* (2023.01); *G06N 3/08* (2013.01); *G06T 7/11* (2017.01); *G06T 7/30* (2017.01); *G06T 11/003* (2013.01); *G06T 15/08* (2013.01); *G06V 10/454* (2022.01); *G06V 10/82* (2022.01); *G16H 30/40* (2018.01); *G06T 2207/20081* (2013.01); *G06T 2207/20084* (2013.01); *G06T 2207/30012* (2013.01); *G06V 2201/033* (2022.01)

(58) Field of Classification Search
CPC ............................................ G06T 2207/30012
See application file for complete search history.

(56) References Cited

U.S. PATENT DOCUMENTS

| | | | |
|---|---|---|---|
| 8,160,322 B2 | 4/2012 | Dikmen et al. | |
| 8,406,494 B2 | 3/2013 | Zhan et al. | |
| 2006/0002615 A1* | 1/2006 | Fu | G06T 7/33 382/254 |
| 2008/0159612 A1* | 7/2008 | Fu | G06T 11/008 382/131 |
| 2011/0286630 A1* | 11/2011 | Harder | G06T 19/00 382/128 |

(Continued)

*Primary Examiner* — Hadi Akhavannik

(57) ABSTRACT

A system and method include identification of a plurality of sub-volumes of an image volume, each of the plurality of sub-volumes of the image volume associated with a respective one of a plurality of vertebra, registration of each of the plurality of sub-volumes of the image volume to one of a plurality of reference sub-volumes associated with a same respective vertebra, input of the registered sub-volumes and the image volume to a trained neural network, reception of an output image volume from the trained neural network, the output image volume labeled to associate voxels with respective vertebra, and display of the output image volume.

20 Claims, 13 Drawing Sheets

(56) References Cited

U.S. PATENT DOCUMENTS

| | | | |
|---|---|---|---|
| 2012/0275670 A1* | 11/2012 | Joglekar | G06T 7/33 |
| | | | 382/128 |
| 2017/0084022 A1* | 3/2017 | Naidu | A61B 8/5223 |
| 2017/0112575 A1* | 4/2017 | Li | A61B 34/10 |
| 2018/0260951 A1* | 9/2018 | Yang | G16H 30/40 |
| 2018/0260957 A1* | 9/2018 | Yang | G06T 7/143 |
| 2019/0015059 A1* | 1/2019 | Itu | G06F 16/285 |
| 2019/0350657 A1* | 11/2019 | Tolkowsky | A61B 6/12 |

* cited by examiner

SPINE SEGMENTATION SYSTEM

CROSS-REFERENCE TO RELATED APPLICATIONS

The present application is related to and claims priority to U.S. Provisional Patent Application No. 62/890,801 filed Aug. 23, 2019, the contents of which are incorporated by reference in their entirety, for all purposes.

BACKGROUND

Conventional medical imaging systems are capable of generating high-quality images of internal structures and processes. The various available imaging modalities each exhibit particular strengths and weaknesses with respect to the type of imaged material, speed of imaging, cost of imaging, etc. Regardless of imaging modality, it is often desirable to identify structures present in an acquired image and the voxels (or pixels) which correspond to the identified structures.

Segmentation is the process of identifying physical boundaries within an image. Segmentation may also include identification of a structure circumscribed by an identified physical boundary. Current segmentation techniques involve the use of features, thresholds and/or models.

Current segmentation techniques suffer from inaccuracy, particularly at the voxel level. It has been considered to train an artificial neural network to perform segmentation. These efforts are hampered by the lack of training data and the wide variance in how a same structure might be depicted in images of different patients (or a same patient). Efficient systems to segment structures within images are desired, particularly in the case of spinal structures.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments train a neural network to recognize vertebra-specific image voxels. The network is trained based on training images from which a sub-volume containing each vertebra is extracted and registered against a corresponding reference vertebrae sub-volume. Each sub-volume is therefore standardized for training, and the need to train the network against vertebrae of all different orientations is reduced. Training the network against a reduced space facilitates efficient learning of an accurate algorithm.

Figure 1:
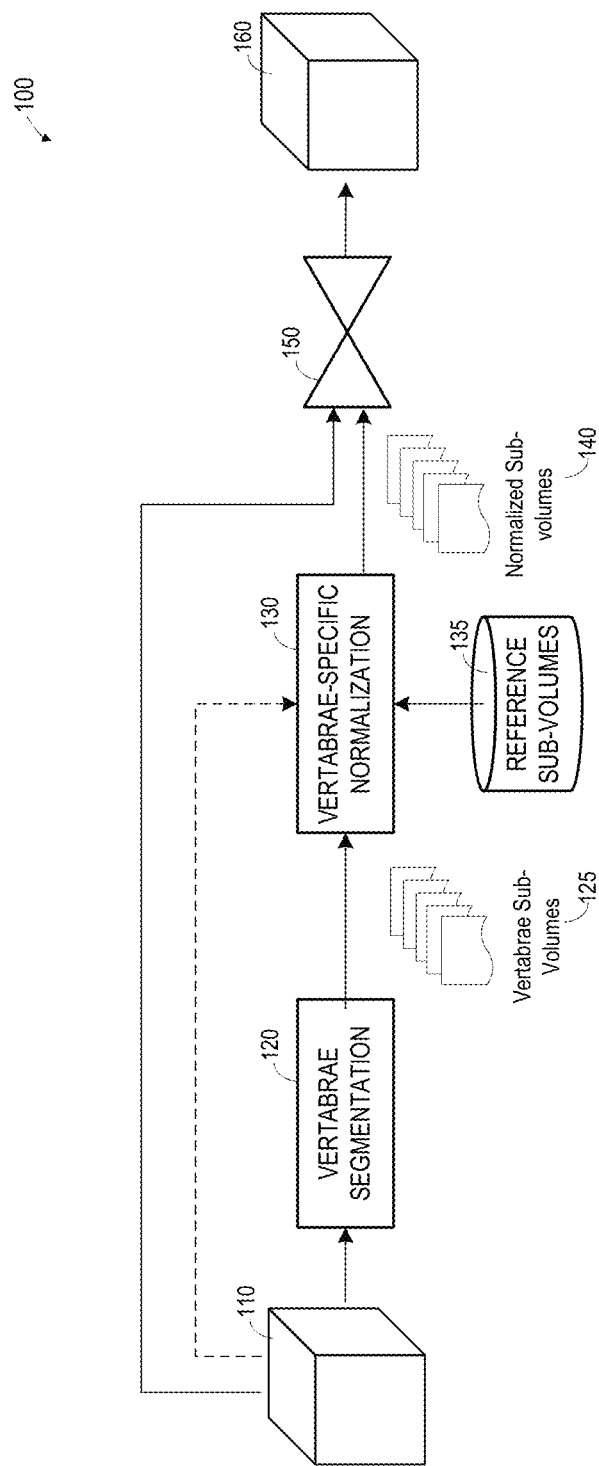
FIG. 1 is a block diagram of a system to segment vertebrae from an image volume using a trained neural network according to some embodiments.

FIG. 1 illustrates system 100 to segment vertebrae from image volume 110 using trained neural network 150. Each component of system 100 may be implemented using any suitable combination of hardware and/or software, and elements of two or more components may be implemented by a same combination of hardware and/or software.

Network 150 may comprise any type of learning network that is or becomes known. Broadly, network 150 may comprise a network of neurons which receive input, change internal state according to that input, and produce output depending on the input and internal state. The output of certain neurons is connected to the input of other neurons to form a directed and weighted graph. The weights as well as the functions that compute the internal state can be modified via training as will be described below. Network 150 may comprise any one or more types of artificial neural network that are or become known, including but not limited to convolutional neural networks, recurrent neural networks, long short-term memory networks, deep reservoir computing and deep echo state networks, deep belief networks, and deep stacking networks.

Image volume 110 may conform to any image format that is or becomes known. Image volume 110 may be reconstructed from data acquired using any imaging modality, including but not limited to Computed Tomography (CT), Magnetic Resonance (MR), Positron-emission Tomography (PET), Single-photon Emission Computed Tomography (SPECT) and ultrasound. According to the present examples, image volume 110 depicts a plurality of individual vertebrae. Embodiments are not limited to use with respect to vertebrae.

Vertebrae segmentation component 120 identifies sub-volumes of image volume 110 which contain respective vertebrae. For example, vertebrae segmentation component 120 may define sub-volumes 125 of volume 110 which correspond to each one of the vertebrae depicted within image volume 110. Each of sub-volumes 125 may be defined as vertices of a rectangular volume containing a respective vertebra.

Vertebrae-specific normalization component 130 normalizes each of sub-volumes 125 based on respective ones of reference sub-volumes 135 to generate normalized sub-volumes 140. For purposes of the example of FIG. 1, normalization is deemed to include transformation of each of sub-volumes 125 to a coordinate space of a corresponding one of reference sub-volumes 135 as well as normalizing sub-volumes 125 to an input size expected by network 150.

In one example, each sub-volume 125 denotes the vertebra contained therein (e.g., L3, T10, C6). For a given sub-volume 125, vertebrae-specific normalization component 130 determines a reference sub-volume 135 corresponding to the vertebrae of the given sub-volume 125. Next, component 130 determines a transform from the coordinate system of the given sub-volume 125 to the coordinate system of the determined reference sub-volume 135 and applies the transform to the given sub-volume 125.

The transformed sub-volume is then sampled so as to result in a normalized sub-volume 140 of the expected size. The transforming and sampling processes are applied to each of sub-volumes 125. It should be noted that each of reference sub-volumes 135 may be associated with different coordinate system, resulting in different transforms being applied to their respective sub-volumes 125. According to some embodiments, each of sub-volumes 125 is sampled as described prior to application of the respective transform.

Trained network 150 receives image volume 110 and normalized sub-volumes 140 as input and outputs image volume 160. According to some embodiments, each voxel of image volume 160 which does not represent a vertebra is assigned a zero value, and each voxel of image volume 160 which represents a vertebra is assigned a value associated with the vertebra. For example, all voxels associated with L3 are assigned a same value, and all voxels associated with L5 are assigned a same value which is different from the value assigned to the L3 voxels.

Figure 2:
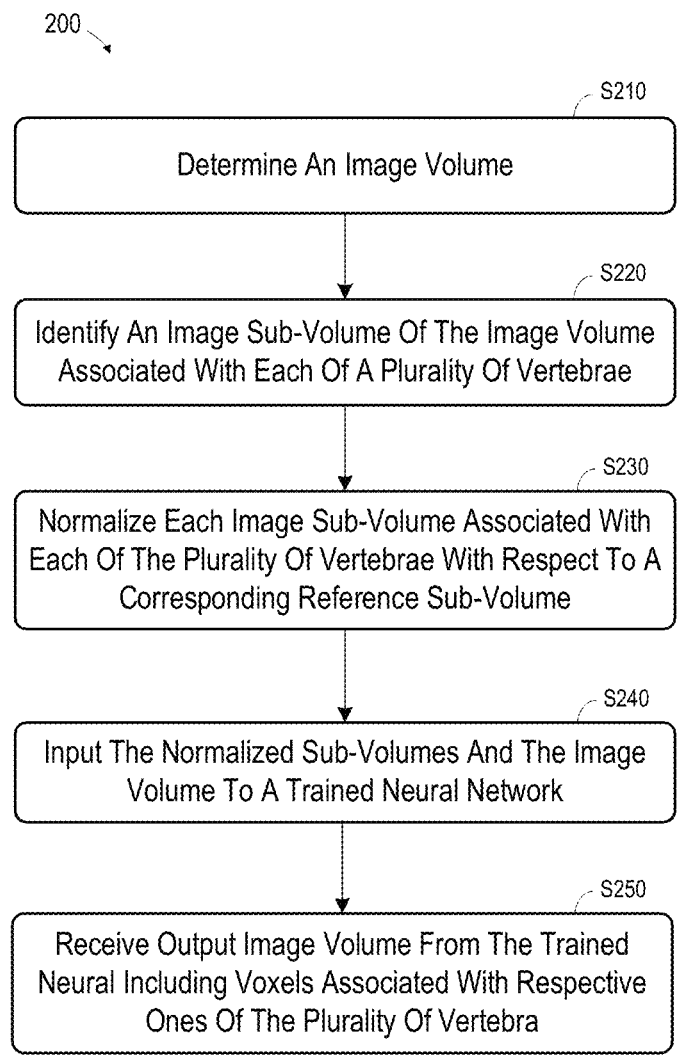
FIG. 2 is a flow diagram of a process to segment vertebrae from an image volume using a trained neural network according to some embodiments.

FIG. 2 is a flow diagram of process 200 to segment vertebrae from an image volume using a trained neural network according to some embodiments. Process 200 and the other processes described herein may be performed using any suitable combination of hardware and software. Software program code embodying these processes may be stored by any non-transitory tangible medium, including a fixed disk, a volatile or non-volatile random access memory, a DVD, a Flash drive, or a magnetic tape, and executed by any one or more processing units, including but not limited to a microprocessor, a microprocessor core, and a microprocessor thread. Embodiments are not limited to the examples described below.

Figure 3:
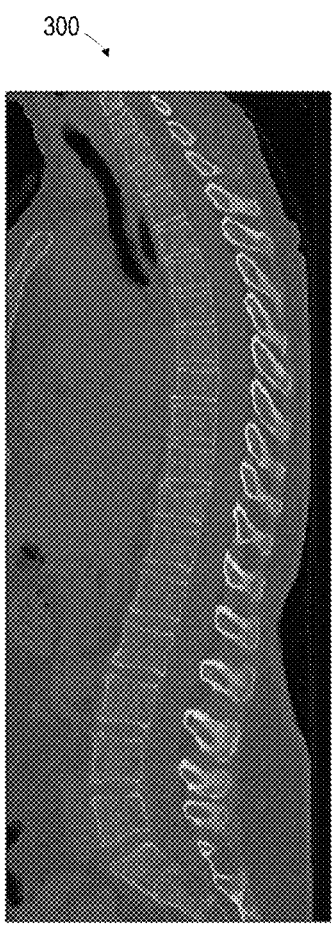
FIG. 3 is a two-dimensional representation of a three-dimensional image volume.

An image volume is initially determined at S210. The image may be acquired from a storage device or using an imaging system. According to one example, a patient is subjected to a CT scan which acquires a plurality of projection images. An image volume is reconstructed from the projection images at S210. FIG. 3 is a two-dimensional representation of an example CT image volume according to some embodiments.

Figure 4:
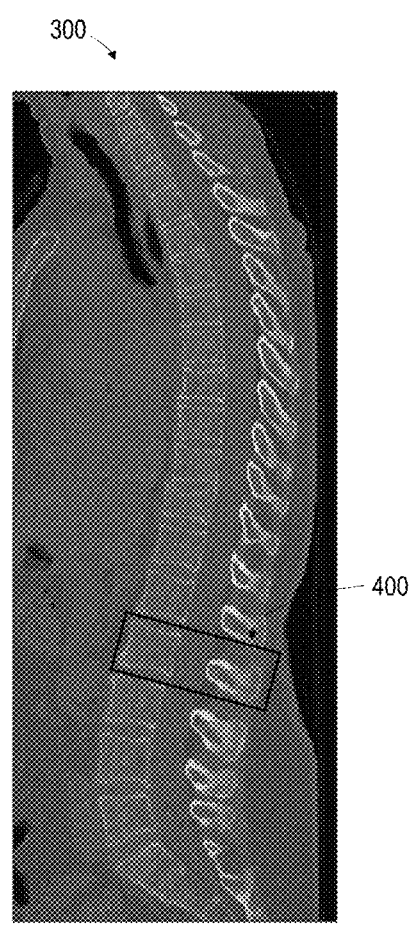
FIG. 4 is a two-dimensional representation of a three-dimensional image volume and a superimposed bounding box according to some embodiments.

An image sub-volume of the image volume is identified for each of a plurality of vertebrae at S220. S220 may include application of known techniques to the image volume to generate coordinates defining sub-volumes including each of the vertebrae depicted in the image volume. According to some embodiments, the coordinates of each sub-volume include the eight vertices of a rectangular "bounding box" surrounding a respective vertebra, and a center coordinate of the bounding box. FIG. 4 is a two-dimensional representation of the FIG. 3 image volume, showing superimposed bounding box 400 surrounding vertebra L4. Embodiments are not limited to rectangular sub-volumes.

Next, at S230, each image sub-volume is normalized with respect to a corresponding reference sub-volume. As described above, S230 may comprise determination of vertebra associated with a sub-volume, determination of a reference sub-volume 135 corresponding to the vertebrae, determination of a transform from the coordinate system of the sub-volume to the coordinate system of the determined reference sub-volume, and application of the transform to the sub-volume.

Figure 5:
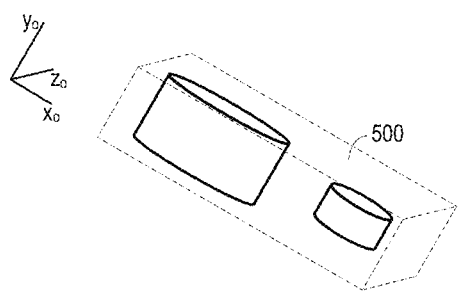
FIG. 5 illustrates an image sub-volume including a vertebra according to some embodiments.

FIG. 5 illustrates sub-volume 500 according to some embodiments. Sub-volume 500 depicts a single vertebra (e.g., L4) and is oriented with respect to coordinate system $(x_0, y_0, z_0)$. It will be assumed that reference sub-volume 600 also depicts L4 and therefore corresponds to sub-volume 500. As shown, reference sub-volume is oriented with respect to coordinate system $(x_1, y_1, z_1)$. According to some embodiments of S230, a transform from coordinate system $(x_0, y_0, z_0)$ to coordinate system $(x_1, y_1, z_1)$ is determined and applied to sub-volume 500, resulting in transformed sub-volume 700 of FIG. 7. Transformed sub-volume 700 conforms to coordinate system $(x_1, y_1, z_1)$.

Figure 6:
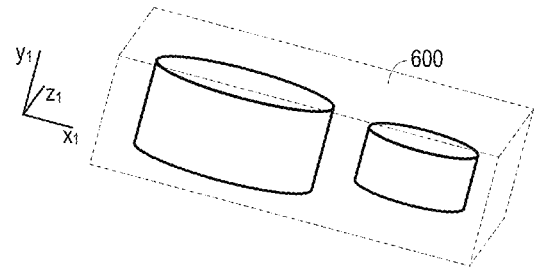
FIG. 6 illustrates a reference sub-volume including a reference vertebra according to some embodiments.
Figure 7:
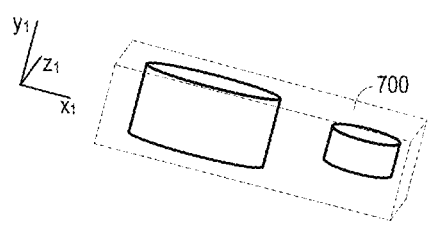
FIG. 7 illustrates an image sub-volume transformed based on the FIG. 6 reference sub-volume according to some embodiments.

The process illustrated in FIGS. 5-7 is performed for each determined sub-volume. In this regard, each sub-volume may be oriented with respect to any coordinate system and a corresponding reference sub-volume may be oriented with respect to any coordinate system. Accordingly, a different transform may be applied to any two or more sub-volumes at S230.

Normalization at S230 may further include sampling the transformed sub-volume to an input size expected by a trained neural network. As also mentioned above, the sub-volumes may be sampled to the expected size prior to application of the respective transform.

The normalized sub-volumes and the original image volume are input to a trained network at S240. Next, at S250, an output image volume is received from the trained neural network. The output image volume includes voxels associated with respective ones of the plurality of vertebrae. For example, each voxel of the output image volume which does not represent a vertebra is assigned a zero value, and each voxel of the output image volume which represents a vertebra is assigned a value associated with the vertebra.

Figure 8:
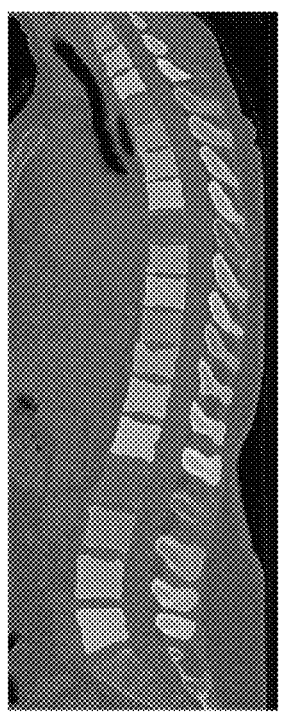
FIG. 8 is a two-dimensional representation of a three-dimensional image volume including vertebra-specific labeled voxels according to some embodiments.

The voxel values of the output image volume may be used to generate another image volume. For example, each voxel value associated with a given vertebra may be associated with a same color and/or intensity (which is unique to each vertebra) and each voxel having a zero value may be considered as transparent. The resulting image volume may be overlaid upon the original image volume to clearly depict each vertebra within the anatomy otherwise depicted in the original image. FIG. 8 is a two-dimensional representation of image 800 according to this example, in which each vertebra is depicted by a different grayscale value.

Figure 9:
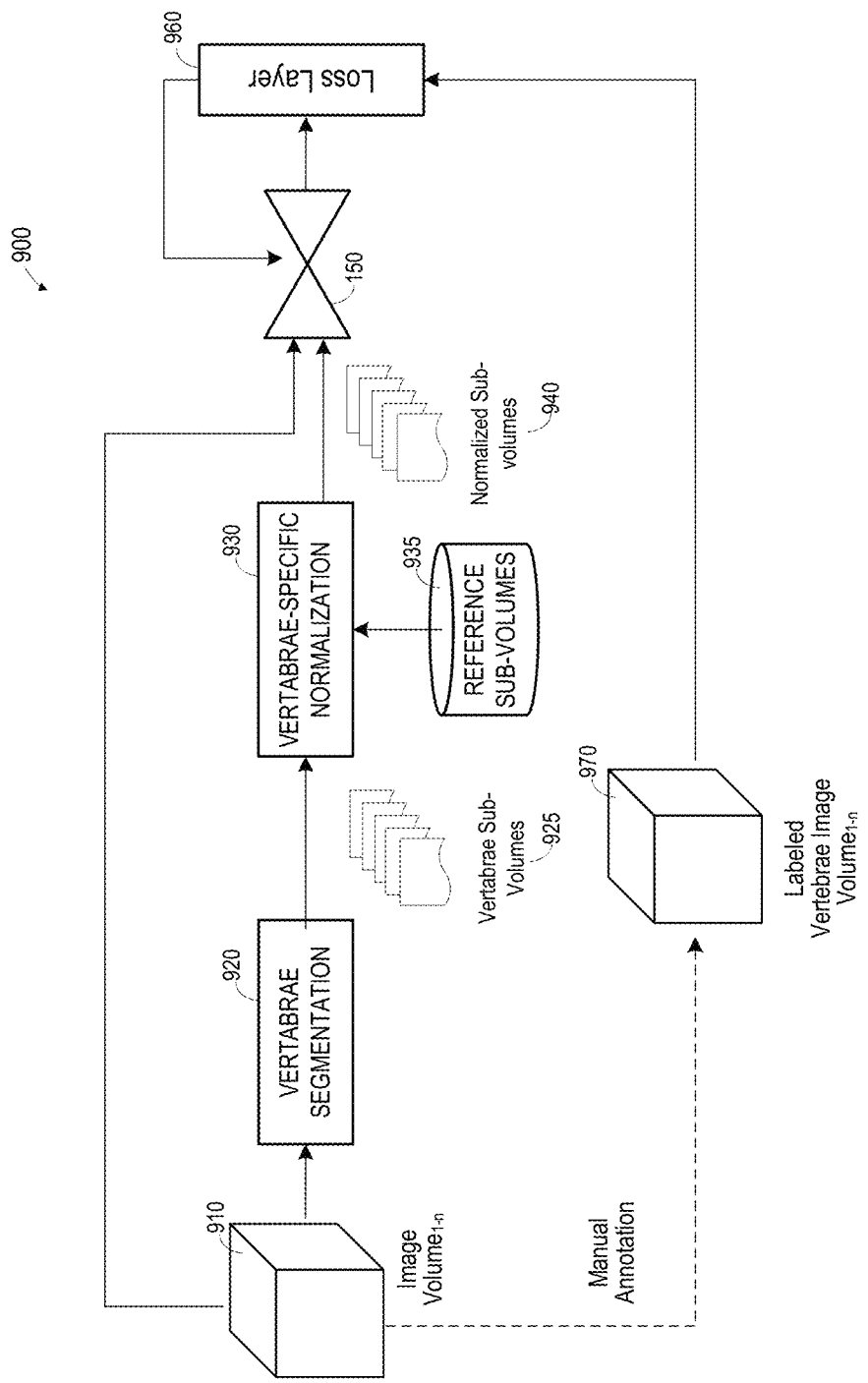
FIG. 9 is a block diagram of a system train a neural network to segment vertebrae from an image volume according to some embodiments.

FIG. 9 depicts architecture 900 to train network 150 for use in system 100 and/or process 200 as described above. Generally, architecture 900 trains network 150 to implement a function. The training is based on training image volumes 910 and corresponding ground truth image volumes 970 including labeled vertebrae.

Image volumes 910 may be acquired from any one or more image volume repositories. In order to increase robustness of the learned function, the number of image volumes 910 may increased by applying a shift and/or rotation to an acquired image volume, and/or applying any suitable image processing (e.g., shear) thereto.

Each of image volumes 910 corresponds to one of image volumes 970. For a given image volume 910, its corresponding image volume 970 is labeled such that each voxel of the given image volume 910 which does not represent a vertebra is assigned a zero value, and each voxel of the given image volume 910 which represents a vertebra is assigned a value associated with the vertebra.

During training, components 920, 930, and 935 may operate on each image volume 910 as described above in conjunction with similarly-named components of FIG. 1. That is, vertebrae segmentation component 920 identifies sub-volumes 925 of the image volume 910 which contain respective vertebrae. Vertebrae-specific normalization component 930 normalizes each of sub-volumes 125 based on respective ones of reference sub-volumes 935 to generate normalized sub-volumes 940, and network 150 receives the image volume 910 and normalized sub-volumes 940 as input and outputs an image volume.

The above process is performed for each n image volume 910, and loss layer 960 determines a loss based on all n image volumes output by network 150 and corresponding labeled image volumes 970. Generally, the determined loss reflects a difference between the n image volumes output by network 150 and corresponding ones of labeled image volumes 970. As is known in the art, the loss is back-propagated to network 150 in order to modify network 150 in an attempt to minimize the loss.

The process repeats and network 150 is iteratively modified in this manner until the loss reaches acceptable levels or training otherwise terminates (e.g., due to time constraints or to the loss asymptotically approaching a lower bound). Further details regarding determination of the loss according to some embodiments are provided below with respect to FIG. 16.

Figure 10:
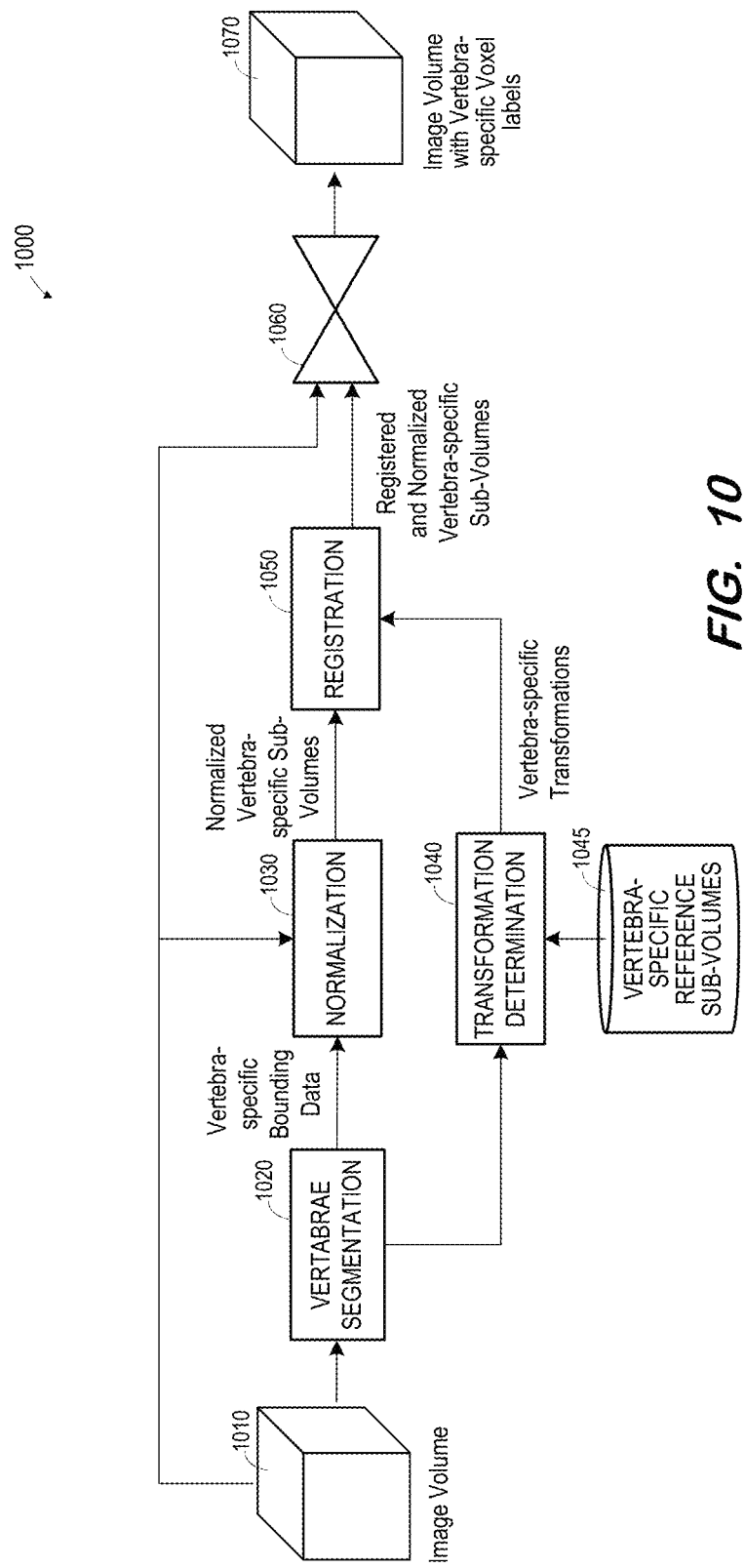
FIG. 10 is a block diagram of a system to segment vertebrae from an image volume using a trained neural network according to some embodiments.

FIG. 10 illustrates system 1000 to segment vertebrae from image volume 1010 using trained neural network 1060 according to some embodiments. System 100 may comprise an implementation of system 100 of FIG. 1, but embodiments are not limited thereto.

Image volume 1010 depicts a plurality of individual vertebrae of a patient and may comprise a reconstructed CT volume. Vertebrae segmentation component 1020 identifies sub-volumes of image volume 1020 which contain respective vertebrae using any suitable system that is or becomes known. Vertebrae segmentation component 1020 outputs sub-volume bounding data specific to each sub-volume (i.e., specific to each vertebra).

Vertebrae-specific normalization component 1030 normalizes each of the sub-volumes identified by the sub-volume bounding data. For example, normalization component 1030 may use the bounding data to re-sample image volume 1010 in view of an expected sub-volume size.

In parallel, transformation determination component 1040 receives the vertebra-specific bounding data from vertebrae segmentation component 1020 and identifies a vertebra-specific reference sub-volume 1045 corresponding to each segmented sub-volume. For each segmented sub-volume, transformation determination component 1040 determines a transform from the coordinate system of the sub-volume to the coordinate system of the determined reference sub-volume 1045 and transmits the transform to registration component.

Registration component 1050 applies the transform determined for each sub-volume to the corresponding normalized sub-volume. The thusly-registered and normalized sub-volumes are input to trained network 1060 along with image volume 1010. Trained network 1060 and outputs image volume 1070 including vertebra-specific voxel labels. According to some embodiments, each voxel of image volume 1070 which does not represent a vertebra is assigned a zero value, and each voxel which represents a vertebra is assigned a value associated with the vertebra.

Figure 11:
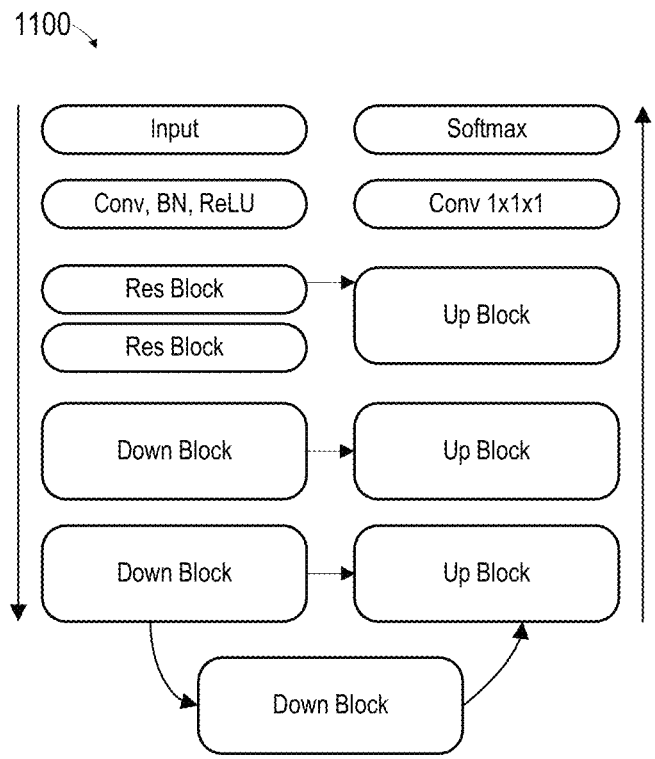
FIG. 11 is a block diagram of a neural network architecture according to some embodiments.

FIG. 11 is a block diagram of the architecture of a neural network according to some embodiments. Architecture 1100 may be used to implement network 150 of FIG. 1 and/or network 1060 of FIG. 10, but embodiments are not limited thereto.

Figure 12:
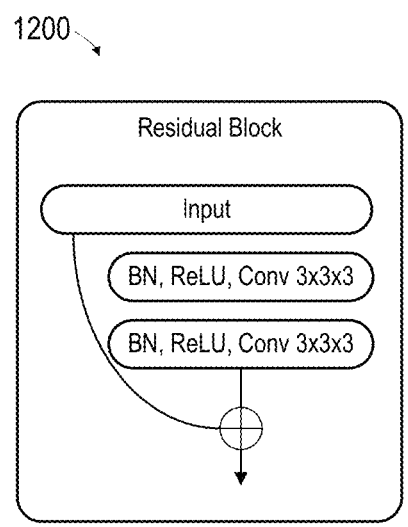
FIG. 12 is a block diagram of a residual block architecture according to some embodiments.
Figure 13:
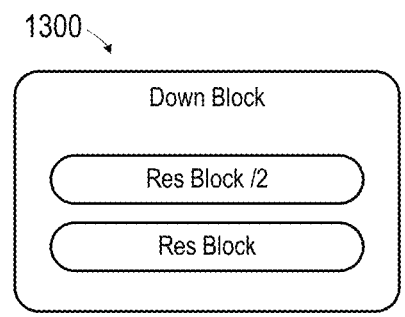
FIG. 13 is a block diagram of a down block architecture according to some embodiments.
Figure 14:
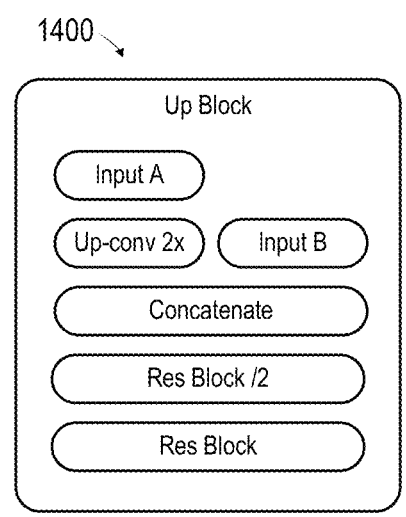
FIG. 14 is a block diagram of an up block architecture according to some embodiments.

Architecture 1100 is a residual U-net which may present an input size of 64 by 64 by 64 voxels and a depth of 5 blocks. FIG. 12 provides a more detailed representation of each Residual Block 1200 depicted in FIG. 11 according to some embodiments. Similarly, FIG. 13 illustrates the composition of each Down Block 1300 of architecture 1100 based on a Residual Block 1200 as shown in FIG. 12. FIG. 14 depicts an embodiment of each Up Block 1300 of FIG. 11, which also may consist of implementations of Residual Block 1200.

Figure 15:
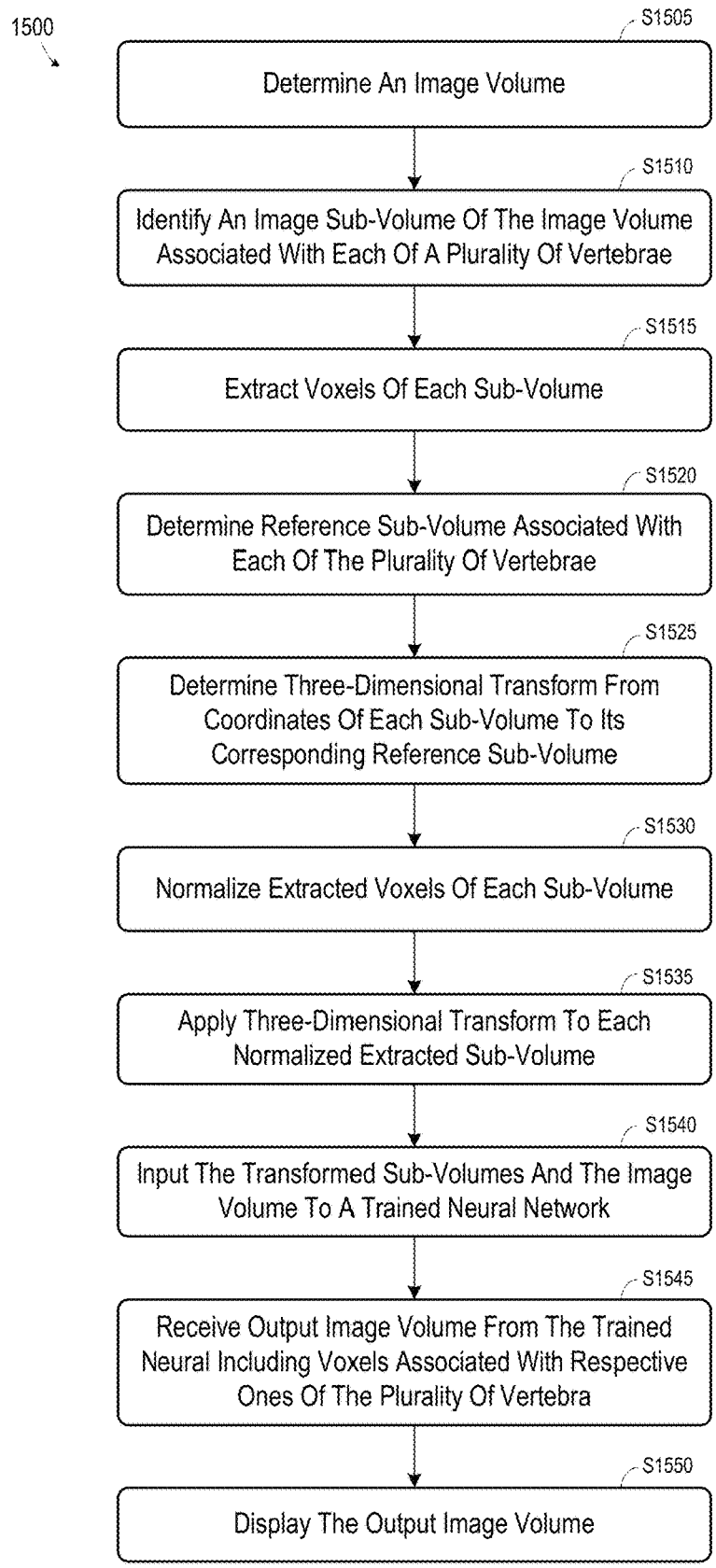
FIG. 15 is a flow diagram of a process to segment vertebrae from an image volume using a trained neural network according to some embodiments.

FIG. 15 is a flow diagram of process 1500 to segment vertebrae from an image volume using a trained neural network according to some embodiments. Process 1500 may be implemented by system 1000, but embodiments are not limited thereto.

An image volume depicting a plurality of vertebrae is determined at S1505. Next, an image sub-volume associated with each of the plurality of vertebrae is determined at S1510. In one example, vertebrae segmentation component 1020 identifies the sub-volumes at S1510 using any suitable system that is or becomes known and outputs sub-volume bounding data specific to each sub-volume.

Voxels of each sub-volume are extracted at S1515. The voxels may be extracted from original image volume 1010 by vertebrae-specific normalization component 1030 based on sub-volume bounding data provided by vertebrae segmentation component 1020.

A reference sub-volume corresponding to each of the identified sub-volumes is determined at S1520, and a three-dimensional transform from coordinates of each sub-volume to coordinates of a corresponding reference sub-volume are determined at S1525. As described above, transformation determination component 1040 may receive sub-volume bounding data from vertebrae segmentation component 1020 and identify a reference sub-volume 1045 corresponding to (i.e., associated with a same vertebra as) each segmented sub-volume. Transformation determination component 1040 may then determine a transform from the coordinate system of the sub-volume to the coordinate system of the corresponding reference sub-volume 1045.

The voxels of each sub-volume extracted at S1515 are normalized at S1530. Normalization component 1030 may normalize the number of voxels in each dimension to conform to an input size expected by network 1060.

The transform determined for each sub-volume is applied to the corresponding normalized sub-volume at S1535. Registration component 1050 may apply the transform determined for each sub-volume to the corresponding normalized sub-volume at S1535.

The transformed sub-volumes and the original image volume are input to a trained network at S1540. Next, at S1545, and by virtue of the training of the network, an output image volume is received. The output image volume includes voxels associated with respective ones of the plurality of vertebra.

The output image volume is displayed at S1550. According to some embodiments, each voxel of image volume 1070 which does not represent a vertebra is displayed as a zero value (e.g., black), and each voxel which represents a particular vertebra is displayed as a grayscale or color value which is uniquely associated with the particular vertebra.

The output image volume may be used to generate another image volume which is displayed at S1550. In some embodiments such as that depicted in FIG. 8, each voxel value associated with a given vertebra is associated with a same grayscale value and each voxel having a zero value may be considered as transparent, and the resulting image volume is overlaid upon the original image volume to depict each vertebra within the anatomy otherwise depicted in the original image.

Figure 16:
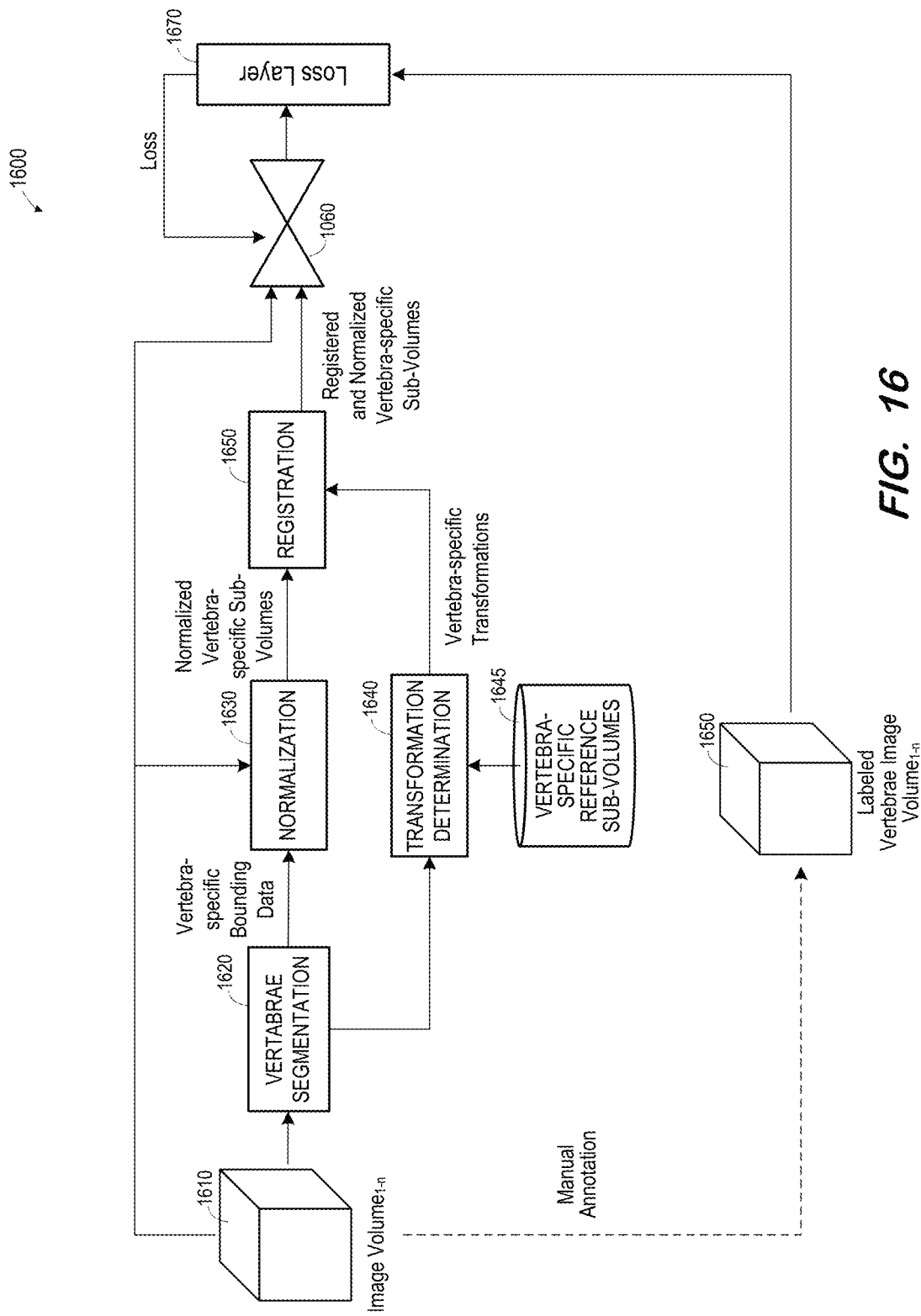
FIG. 16 is a block diagram of a system to train a neural network to segment vertebrae from an image volume according to some embodiments.

FIG. 16 depicts architecture 1600 to train network 1060 for use in system 1000 and/or process 1500 as described above.

As described above, image volumes 1610 may be acquired from any one or more image volume repositories, and may include image volumes generated based on other image volumes. Each of image volumes 1610 corresponds to one of image volumes 1650. Each image volume 1650 is manually annotated to assign a zero value to each voxel of its corresponding image volume 1610 which does not depict a portion of avertebra, and a vertebra-specific value to each voxel of its corresponding image volume 1610 which depicts a portion of vertebra.

During training, components 1620, 1630, 1640 and 1650 operate on each image volume 1610 as described above in conjunction with similarly-named components of FIG. 10. Specifically, vertebrae segmentation component 1620 identifies sub-volumes of the image volume 1610 which contain respective vertebrae. Vertebrae-specific normalization component 1630 normalizes each of the sub-volumes based on an input size expected by network 1060, transformation determination component 1640 determines a transform for each sub-volume based on respective ones of reference sub-volumes 1645, and registration component 1650 applies corresponding transforms to each normalized sub-volume. The registered normalized sub-volumes are input to network 1060 along with the image volume 1610, and network 1060 outputs a vertebrae-specific-labeled image volume. The above process is performed for all n image volumes 1610.

Loss layer 1670 determines a loss based on all n image volumes output by network 1060 and on corresponding labeled image volumes 1650. Generally, the determined loss reflects a difference between the n image volumes output by network 150 and corresponding ones of labeled image volumes 970. As is known in the art, the loss is back-propagated to network 1060 in order to modify network 1060 in an attempt to minimize the loss, and the process repeats to iteratively modify network 1060 until the loss reaches acceptable levels or training otherwise terminates.

According to some embodiments, the loss function determined by loss layer 1670 includes a Dice objective function. The Dice coefficient measures the degree of overlap between two sets. For two binary sets (ground truth (G) and predicted class membership (P)) with (N) elements each, the Dice coefficient can be written as:

$$D = \frac{2\sum_i^N p_i g_i}{\sum_i^N p_i + \sum_i^N g_i}$$

where each $p_i$ and $g_i$ are binary labels. $p_i$ in [0, 1] is set from the softmax layer representing the probability that the $i^{th}$ voxel is in the foreground class. Each $g_i$ is obtained from a one-hot encoding of the ground-truth labeled volume class. For model evaluation, class labels may be assigned binary labels from the most likely class per voxel.

The loss function may further include a weighted false-positive/false-negative loss term to provide smoother convergence, such that losses closer to the edge of a vertebra boundary are given greater weight:

$$L_{FNFP} = \sum_{i \in I} w_i p_i (1 - g_i) + \sum_{i \in I} w_i (1 - p_i) g_i$$
$$w_i = \gamma_e \exp(-d_i^2/\sigma) + \gamma_c f_i,$$

where $d_i$ is the Euclidean distance to the nearest class boundary, $f_i$ is the frequency of the ground truth class at voxel i. According to some embodiments, σ is set to 10 voxels, and $\gamma_e$ and $\gamma_c$ are set to 5 and 2, respectively.

A total loss may be determined as a weighted combination of the weighted loss above and the Dice coefficient as follows:

$$L = L_{FNFP} + \alpha L_D,$$

where α may be initially set to 0.5 and incrementally lowered throughout training.

Figure 17:
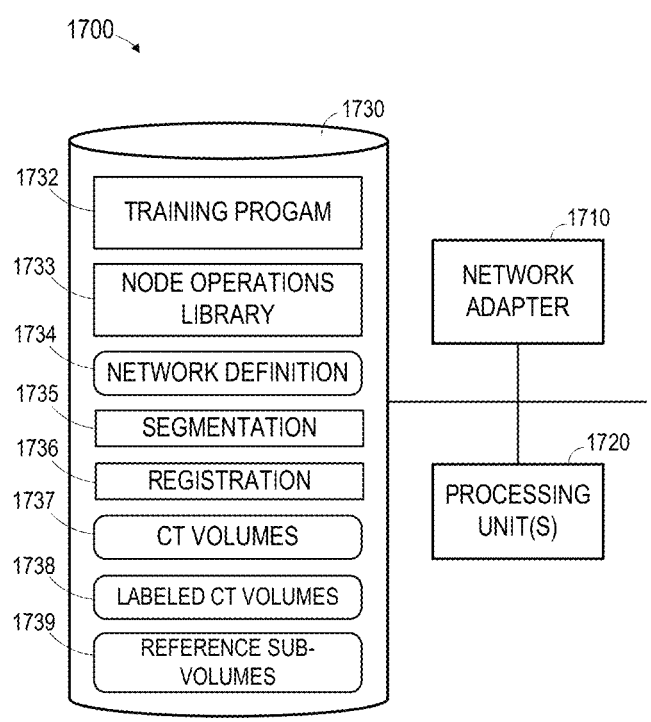
FIG. 17 is a block diagram of an apparatus to execute neural network training according to some embodiments.

FIG. 17 illustrates computing system 1700 according to some embodiments. System 1700 may comprise a computing system to facilitate the design and training of a network as is known in the art. Computing system 1700 may comprise a standalone system, or one or more elements of computing system 1700 may be located in the cloud.

System 1700 includes network adapter 1710 to communicate with external devices via a network connection. Processing unit(s) 1720 may comprise one or more processors, processor cores, or other processing units to execute processor-executable program code. In this regard, storage system 1730, which may comprise one or more memory devices (e.g., a hard disk drive, a solid-state drive), stores processor-executable program code of training program 1732 which may be executed by processing unit(s) 1720 to train a network as described herein.

Training program 1732 may utilize node operations library 1733, which includes program code to execute various operations associated with node operations as defined in node operations library 1733. According to some embodiments, computing system 1700 provides interfaces and development software (not shown) to enable development of training program 1732 and generation of network definition 1734.

Storage device 1740 also includes program code of segmentation component 1735, and registration component 1736 as described herein. This program code may be executed in conjunction with stored CT volumes 1737, ground truth labeled CT volumes 1738 reference sub-volumes 1739 and training program 1732 as described above to train a network defined by network definition 1734.

Figure 18:
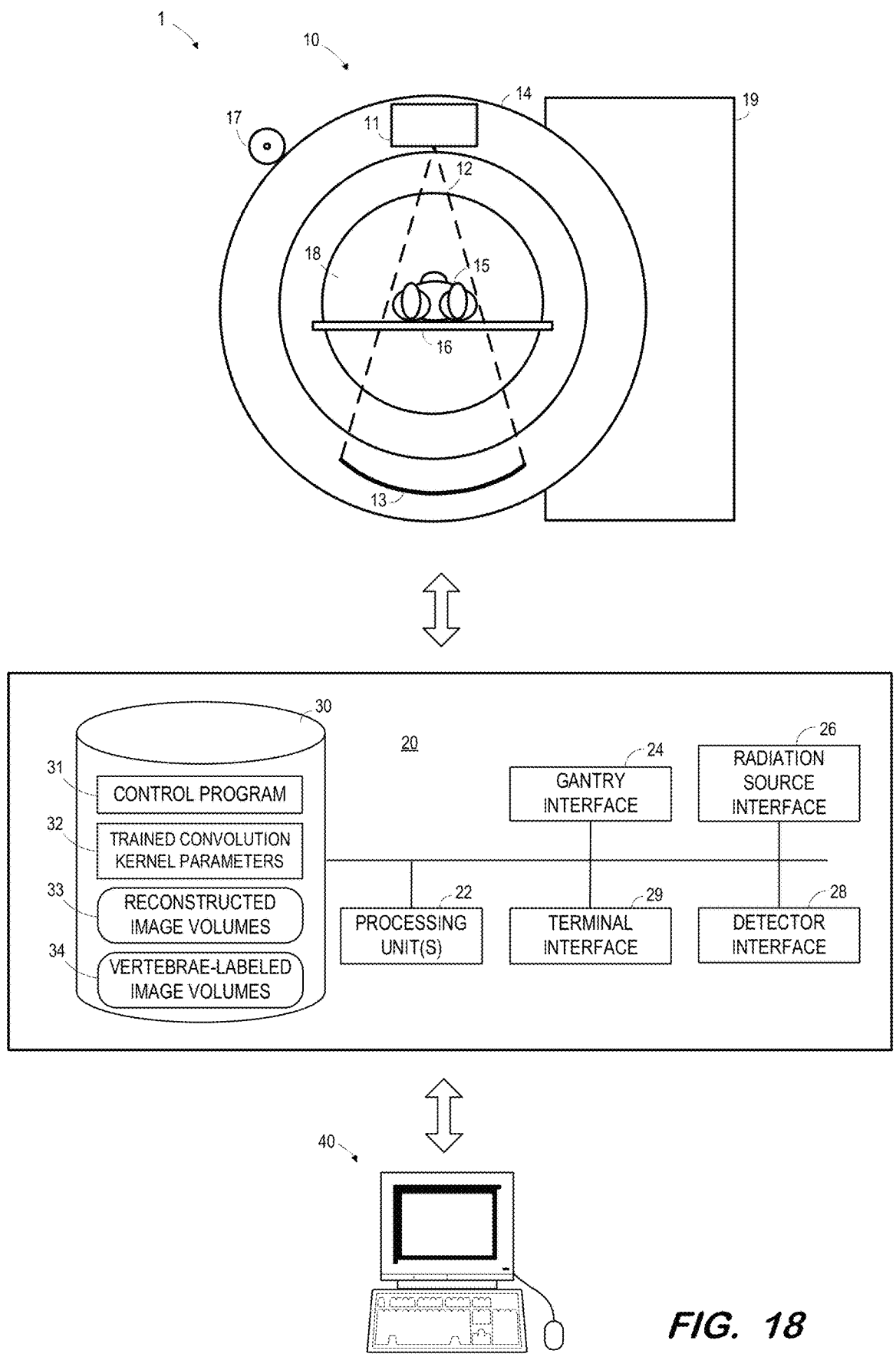
FIG. 18 illustrates an imaging system utilizing a trained neural network to segment vertebrae according to some embodiments.

FIG. 18 illustrates system 1 according to some embodiments. System 1 may be operated to acquire CT data and generate vertebrae-labeled CT volumes according to some embodiments. Embodiments are not limited to system 1.

System 1 includes X-ray imaging system 10, control and processing system 20, and operator terminal 40. Generally, and according to some embodiments, X-ray imaging system 10 acquires two-dimensional X-ray images of a patient, and control and processing system 20 controls X-ray imaging system 10 and receives the acquired images therefrom. Control and processing system 20 reconstructs a CT volume based on the acquired images and generates a vertebrae-labeled CT volume therefrom using a trained neural network as described above. Such processing may be based on user input received by terminal 40 and provided to control and processing system 20 by terminal 40.

Imaging system 10 comprises a CT scanner including X-ray source 11 for emitting X-ray beam 12 toward opposing radiation detector 13. Embodiments are not limited to CT data or to CT scanners. X-ray source 11 and radiation detector 13 are mounted on gantry 14 such that they may be rotated about a center of rotation of gantry 14 while maintaining the same physical relationship therebetween.

Radiation detector 13 may comprise any system to acquire an image based on received X-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

To generate X-ray images, patient 15 is positioned on bed 16 to place a portion of patient 15 between X-ray source 11 and radiation detector 13. Next, X-ray source 11 and radiation detector 13 are moved to various projection angles with respect to patient 15 by using rotation drive 17 to rotate gantry 14 around cavity 18 in which patient 15 is positioned. At each projection angle, X-ray source 11 is powered by high-voltage generator 19 to transmit X-ray radiation 12 toward detector 13. Detector 13 receives the radiation and produces a set of data (i.e., a raw X-ray image) for each projection angle.

System 20 may comprise any general-purpose or dedicated computing system. Accordingly, system 20 includes one or more processing units 22 configured to execute processor-executable program code to cause system 20 to operate as described herein, and storage device 30 for storing the program code. Storage device 30 may comprise one or more fixed disks, solid-state random access memory, and/or removable media (e.g., a thumb drive) mounted in a corresponding interface (e.g., a USB port).

Storage device 30 stores program code of system control program 31. One or more processing units 22 may execute system control program 31 to move gantry 14, to move table 16, to cause radiation source 11 to emit radiation, to control detector 13 to acquire an image, and to perform any other function. In this regard, system 20 includes gantry interface 24, radiation source interface 26 and detector interface 28 for communication with corresponding units of system 10.

System control program 31 may also be executable to reconstruct an image volume 33 from acquired projection images, and pre-process sub-volumes thereof as described above. The image volume and processed sub-volumes may then be input to a network implementing trained convolution kernel parameters 32 to generate vertebrae-labeled image volumes 34.

Terminal 40 may comprise a display device and an input device coupled to system 20. Terminal 50 may display any of projection images, reconstructed volumes 33, sub-volumes, and vertebrae-labeled image volumes 34. Terminal 40 may receive user input for controlling display of the images, operation of imaging system 10, and/or the processing described herein. In some embodiments, terminal 40 is a separate computing device such as, but not limited to, a desktop computer, a laptop computer, a tablet computer, and a smartphone.

Each of system 10, system 20 and terminal 40 may include other elements which are necessary for the operation thereof, as well as additional elements for providing functions other than those described herein.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
a storage device storing a plurality of reference sub-volumes, each of the plurality of reference sub-volumes associated with a respective vertebra; and
a processing unit to execute processor-executable program code to cause the system to:
determine an image volume;
identify a plurality of sub-volumes of the image volume, each of the plurality of sub-volumes of the image volume associated with a respective one of a plurality of vertebra;
for each of the plurality of sub-volumes of the image volume:
determine a coordinate system of a reference sub-volume associated with a same respective vertebra as the sub-volume, the determined coordinate system of a first reference sub-volume being different from the determined coordinate system of a second reference sub-volume;
determine a transform from a coordinate system of the sub-volume of the image volume to the determined coordinate system of the reference sub-volume associated with a same respective vertebra as the sub-volume of the image volume, the determined transform to a coordinate system of a first reference sub-volume being different from the determined transform to a coordinate system of a second reference sub-volume; and
apply the transform to the sub-volume to register the sub-volume to the reference sub-volume associated with a same respective vertebra;
input the registered sub-volumes and the image volume to a trained neural network;
receive an output image volume from the trained neural network, the output image volume labeled to associate voxels with respective vertebra; and
display the output image volume.

2. A system according to claim 1, wherein all voxels of the output image volume associated with a first vertebra are labeled with a first value, and all voxels of the output image volume associated with a second vertebra are labeled with a second value different from the first value.

3. A system according to claim 2, wherein all voxels of the output image volume which are not associated with any vertebra are labeled with a third value different from the first value and the second value.

4. A system according to claim 2, wherein registration of each of the plurality of sub-volumes of the image volume comprises sampling of each of the plurality of sub-volumes of the image volume based on a desired sub-volume size.

5. A system according to claim 1, wherein registration of each of the plurality of sub-volumes of the image volume comprises sampling of each of the plurality of sub-volumes of the image volume based on a desired sub-volume size.

6. A system according to claim 1, wherein the neural network is trained using total loss function comprising a Dice coefficient.

7. A system according to claim 6, wherein the total loss function comprises a weighted loss term.

8. A method to segment vertebrae from an image volume, comprising:
   determining an image volume;
   identifying a plurality of sub-volumes of the image volume, each of the plurality of sub-volumes of the image volume associated with a respective one of a plurality of vertebra,
   for each of the plurality of sub-volumes of the image volume:
      determining a coordinate system of a reference sub-volume associated with a same respective vertebra as the sub-volume, the determined coordinate system of a first reference sub-volume being different from the determined coordinate system of a second reference sub-volume;
      determining a transform from a coordinate system of the sub-volume of the image volume to the determined coordinate system of the reference sub-volume associated with a same respective vertebra as the sub volume of the image volume, the determined transform to a coordinate system of a first reference sub-volume being different from the determined transform to a coordinate system of a second reference sub-volume; and
      registering the sub-volume to the reference sub-volume associated with a same respective vertebra by applying the transform determined for the sub-volume to the sub-volume;
   inputting the registered sub-volumes and the image volume to a trained neural network;
   receiving an output image volume from the trained neural network, the output image volume comprising labels associating voxels with respective vertebra; and
   displaying the output image volume.

9. A method according to claim 8, wherein all voxels of the output image volume associated with a first vertebra are labeled with a first value, and all voxels of the output image volume associated with a second vertebra are labeled with a second value different from the first value.

10. A method according to claim 9, wherein all voxels of the output image volume which are not associated with any vertebra are labeled with a third value different from the first value and the second value.

11. A method according to claim 9, wherein registering each of the plurality of sub-volumes of the image volume comprises sampling each of the plurality of sub-volumes of the image volume based on a desired sub-volume size.

12. A method according to claim 8, wherein registering each of the plurality of sub-volumes of the image volume comprises sampling each of the plurality of sub-volumes of the image volume based on a desired sub-volume size.

13. A method according to claim 8, wherein the neural network is trained using total loss function comprising a Dice coefficient.

14. A system according to claim 13, wherein the total loss function comprises a weighted loss term.

15. An imaging system, comprising:
   a scanner to acquire a plurality of two-dimensional sets of image data;
   a processing unit to:
      reconstruct an image volume based on the plurality of two-dimensional sets of image data;
      identify a plurality of sub-volumes of the image volume, each of the plurality of sub-volumes of the image volume associated with a respective one of a plurality of vertebra;
      for each of the plurality of sub-volumes of the image volume:
         determine a coordinate system of a reference sub-volume associated with a same respective vertebra as the sub-volume, the determined coordinate system of a first reference sub-volume being different from the determined coordinate system of a second reference sub-volume;
         determine a transform from a coordinate system of the sub-volume of the image volume to the determined coordinate system of the reference sub-volume associated with a same respective vertebra as the sub-volume of the image volume, the determined transform to a coordinate system of a first reference sub-volume being different from the determined transform to a coordinate system of a second reference sub-volume; and
         apply the transform determined for the sub-volume to the sub-volume to register the sub-volume to the reference sub-volume associated with a same respective vertebra;
      input the registered sub-volumes and the image volume to a trained neural network; and
      receive an output image volume from the trained neural network, the output image volume labeled to associate voxels with respective vertebra; and
   a display to display the output image volume.

16. A system according to claim 15, wherein all voxels of the output image volume associated with a first vertebra are labeled with a first value, and all voxels of the output image volume associated with a second vertebra are labeled with a second value different from the first value.

17. A system according to claim 16, wherein all voxels of the output image volume which are not associated with any vertebra are labeled with a third value different from the first value and the second value.

18. A system according to claim 16, wherein registration of each of the plurality of sub-volumes of the image volume comprises sampling of each of the plurality of sub-volumes of the image volume based on a desired sub-volume size.

19. A system according to claim 15, wherein registration of each of the plurality of sub-volumes of the image volume comprises sampling of each of the plurality of sub-volumes of the image volume based on a desired sub-volume size.

20. A system according to claim 15, wherein the neural network is trained using total loss function comprising a Dice coefficient and a weighted loss term.

* * * * *